United States Patent [19]

Armbruster

[11] 3,997,519

[45] Dec. 14, 1976

[54] METHOD OF PRODUCING QUATERNARY PYRIDINIUM COMPOUNDS

[75] Inventor: Robert F. Armbruster, Columbia, N.Y.

[73] Assignee: GAF Corporation, New York, N.Y.

[22] Filed: June 20, 1974

[21] Appl. No.: 481,382

Related U.S. Application Data

[63] Continuation of Ser. No. 253,134, May 15, 1972, abandoned.

[52] U.S. Cl. .............................. 260/155; 260/152; 260/154; 260/156; 260/158; 260/163; 260/164; 260/186; 260/187; 260/197; 260/206; 260/207; 260/207.1; 260/207.5; 260/286 R; 260/294.8 R; 260/378; 260/379; 260/567.6 M; 260/567.6 P

[51] Int. Cl.² .............. C09B 43/00; C07D 213/20

[58] Field of Search ............... 260/156, 294.8, 155

[56] References Cited

FOREIGN PATENTS OR APPLICATIONS

| 1,210,821 | 11/1970 | United Kingdom ............... 260/156 |
| 1,211,078 | 11/1970 | United Kingdom ............... 260/156 |
| 1,211,079 | 11/1970 | United Kingdom ............... 260/156 |
| 1,219,981 | 1/1971 | United Kingdom ............... 260/156 |

*Primary Examiner*—Charles F. Warren
*Attorney, Agent, or Firm*—Walter C. Kehm; Marilyn J. Maue

[57] ABSTRACT

The method of preparing quaternary pyridinium compounds having the formula

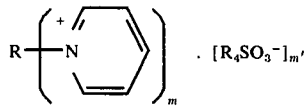

wherein R represents alkyl,

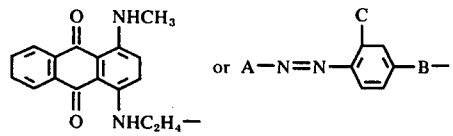

in which A is phenyl, naphthyl, carbostyrilyl, pyrazolinyl and substituted derivatives thereof where the substitutents are selected from the group consisting of alkyl having 1 to 4 carbon atoms, $NO_2$, Cl, Br, phenyl, nitrophenyl and methylsulfonate; B is -O-alkylene-,

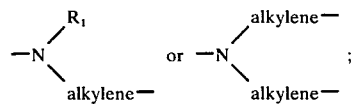

and C is selected from the group consisting of hydrogen, $NHCOR_1$ and, when B is -O-alkylene, C can also be $—OR_2—$ where $R_1$ is alkyl of 1 to 4 carbon atoms and $R_2$ is alkylene of 1 to 4 carbon atoms; and wherein $R_4$ represents lower alkyl having 1 to 6 carbon atoms, halophenyl, alkylphenyl or naphthyl, $m$ represents an integer of 1 or 2 and $m'$ is equal to $m$. The process for preparing the particularly designated compounds above comprises contacting pyridine and a hydroxy-containing compound having the formula: $R'—(OH)_n$ wherein $R'$ represents alkyl,

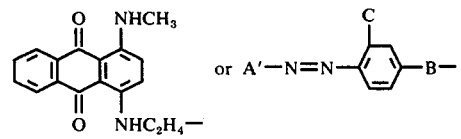

in which A' is phenyl, naphthyl, carbostyrilyl, pyrazolinyl and substituted derivatives thereof where the substituents are selected from the group consisting of alkyl having 1 to 4 carbon atoms, $NO_2$, Cl, Br, phenyl, nitrophenyl and hydroxy; B, C, $R_1$ and $R_2$ are as defined above; and $n$ is an integer of 1 or 2 and is equivalent to $m$ defined above; reacting the pyridine and said hydroxy-containing compound in the presence of a sulfonyl halide having the formula $R_4SO_2X$ wherein $R_4$ is as defined above and X is Cl, Br or F; and conducting the reaction at an elevated temperature up to the reflux temperature of the reaction mixture. The quaternary pyridinium compounds can be used to prepare cationic surfactants, cationic pharmaceuticals, cationic dyestuffs, pesticides, fungicides and agricultural chemicals.

2 Claims, No Drawings

METHOD OF PRODUCING QUATERNARY PYRIDINIUM COMPOUNDS

This is a continuation of application Ser. No. 253,134, filed May 15, 1972, now abandoned.

This invention relates to a novel method of producing quaternary ammonium compounds and more specifically relates to the production of quaternized dyestuffs.

It is known to produce quaternary ammonium compounds by reacting a tertiary amine with an alkylation or arylation agent such as an alkyl halide, benzyl halide, alkyl sulfate or the like.

In JACS 75, 3851–2 (1951), there has been disclosed the reaction of an alcohol, methanesulfonyl chloride and pyridine to form products identified as alkyl methanesulfonates or alkyl chlorides. It is set out in the article that by subsequent reaction there may be formed from the alkyl chloride olefins or alkylpyridinium salts. However, while the article describes in detail the preparation of the alkyl chlorides and olefins, there is no further mention of the production of the alkylpyridinium salts or any means by which the same may be produced. Thus, this article contains no mention or suggestion that a quaternary ammonium product was ever actually produced by the general method disclosed therein.

In JACS 86 (2) 288 (1964), there has been described the reaction of methanol, triethylamine and methanesulfonyl chloride which produces trimethylamine hydrochloride as a solid reaction product. Following filtration, evaporation and distillation of this reaction mixture, the methyl ester of methyl sulfonic acid is recovered.

A number of other reactions involving methanesulfonyl chloride as a reactant have been described. For instance, in J. Org. Chem. 33, 1074 (1968) the following reaction is described:

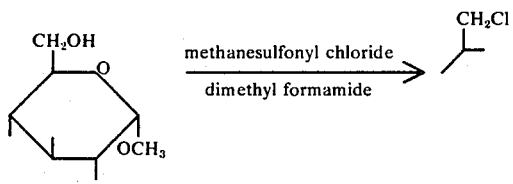

In J. Org. Chem. 27, 1395 (1962) a reaction is hereinafter set out as disclosed in which the chloride is produced

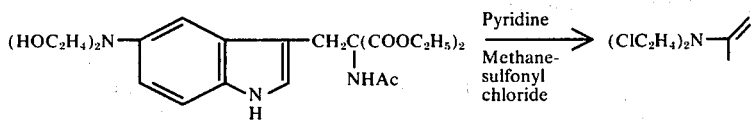

Finally, in J. Org. Chem. 29, 1930 (1964) there is described the preparation of a more unsaturated compound than the starting material as follows:

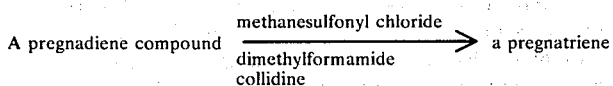

Thus, the art available describes the production of more highly unsaturated compounds, chlorides and esters but there is no enabling disclosure or description of a method for the production of quaternary ammonium compounds.

In accordance with the invention, it has now been found that quaternary ammonium compounds can be easily and simply prepared by reacting a compound containing an alcoholic hydroxyl group with a tertiary amine in the presence of a lower alkyl sulfonyl halide, substituted alkyl halide or an aryl sulfonyl halide, for instance, a bromide or fluoride and preferably a chloride.

In accordance with the invention, the desired quaternary ammonium compound is prepared from the amine, alkyl or aryl sulfonyl halide and alcohol in accordance with the following reaction scheme:

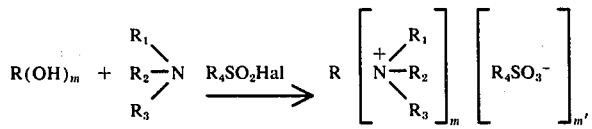

wherein R represents alkyl which can be a substituent of an aryl compound, $R_1$, $R_2$ and $R_3$ each represent substituents which together with the N atom to which they are attached form a tertiary amine, $R_4$ represents lower akyl having from 1 to 6 carbon atoms, phenyl or naphthyl and $m$ represents an integer of the group consisting of 1 and 2 and $m'$ is equal to $m$.

The reaction in accordance with the invention can be employed in the production of quaternary ammonium compounds, the reaction taking place between the alcoholic group containing compound and tertiary amine in the presence of an organic sulfonyl halide. More specifically, the reaction is particularly adapted to the production of cationic dyestuffs, cationic surfactants, cationic pharmaceuticals, pesticides, fungicides and agricultural chemicals in general where cationic substituents are desirable.

In accordance with one aspect of the invention, there is provided a method for producing cationic dyestuffs having the following formula:

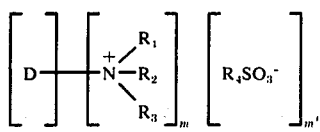

wherein D represents a dyestuff moiety and $R_1$, $R_2$, $R_3$ and $R_4$ $m'$ and $m$ are each as defined above. In this aspect of the invention, D is preferably exemplified by a moiety of an azo dye, azoic dye or anthraquinone dye.

The quaternization process is most particularly advantageously used in the preparation of azo dyes corresponding to the following formula:

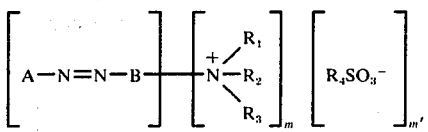

where A represents a diazo moiety and B represents a coupler moiety, A and B both being free of solubilizing sulfonic and carboxylic acid groups; $R_1$, $R_2$, $R_3$, $R_4$ $m'$ and $m$ all being as defined as above.

In accordance with the invention, the following compounds are illustrative of the alcohol $R(OH)_n$ wherein R is alkyl which may be a substituent of an aryl compound and $n$ may be 0, 1 or 2.

methanol
ethanol
propanol
isopropanol
butanol
sec-butanol
tert-butanol
pentanol
hexanol
octanol
1,1,3,3-tertramethylbutanol-1
dodecanol
hexadecanol
octadecanol
glycol
nonylphenoxypoly(ethyleneoxy)ethanol
1-(2-hydroxyethylamino)-4-methylaminoanthraquinone $R(OH)_n$ wherein R and $n$ are as above defined may also represent an azo dyestuff of the formula:

wherein A is a diazo moiety, B a coupler moiety and $m$ is 1 or 2.
In this instance, A may be a mono or diazo group and may be either heterocyclic or non-heterocyclic. More specifically, A may be phenyl, substituted phenyl, phenylazophenyl or phenylazonaphthyl or may represent a heterocyclic moiety. In all cases, however, A is required to be free of solubilizing sulfonic and carboxylic groups. Particularly valuable dyestuffs are those wherein A contains a negative substituent in the para position to the azo linkage.

Compounds wherein $R(OH)_m$ corresponds to the formula $(HO)_nANH_2$ wherein $n$ is as above defined and A is a diazo moiety are exemplified by the following:
aniline
o-, m- and p-toluidine
o-, m- and p-chloroaniline
o-, m- and p-bromoaniline
2,4-dibromoaniline
2,4-dichloroaniline
2,4,6-trichloroaniline
p-nitroaniline
2-chloro-4-nitroaniline
2-bromo-4-nitroaniline
2,6-dichloro-4-nitroaniline
2,4-dibromo-4-nitroaniline
2-cyano-4-nitroaniline
2-cyano-6-chloro(or bromo)-4-nitroaniline
2-methylsulfonyl-4-nitroaniline
p-methylsulfonylaniline
p-phenylsulfonylaniline
p-dimethylsulfonamidoaniline
p-carboethoxyaniline
p-N-ethylcarbamylaniline
4-chloro-α, α, α-trifluoro-o-toluidine
6-ethylsulfonyl-α, α, α-trifluoro-o-toluidine
2-, 3-, and 4-(N-2-hydroxyethylamino)aniline
2-, 3-, and 4-(N-di-2-hydroxyethylamino)aniline
2-chloro(bromo or cyano)-4-(N-2-hydroxyethylamino)aniline
2-chloro(bromo or cyano)-4-(N-di-2-hydroxyethylamino)aniline
2-chloro-4-(N-ethyl-N-2-hydroxyethylamino)aniline
p-[p-(1,1,3,3-tetramethylbutyl)phenoxy]aniline
p-aminoacetophenone
4'-amino-m-tolyl-o-benzotoluidide
5'-amino-2,4-benzoxylidide
4'-amino-6'-methyl-m-benzanisidide
p-aminobenzoic acid, methyl or butyl ester
p-phenylazoaniline
4-o-tolylazo-o-toluidine
6-(2,4-xylylazo)-2,4-xylidine
4-m-tolylazo-m-toluidine
4-phenylazo-1-naphthylamine
2-aminothiazole
2-aminobenzothiazole
2-amino-6-methoxybenzothiazole
2-amino-6-methylbenzothiazole
2-amino-6-methylsulfonylbenzothiazole
2-amino-5,6-dichlorobenzothiazole
2-(p-aminophenyl)-6-methylbenzothiazole
2-(4-amino-m-tolyl)-4,6-dimethylbenzothiazole
2-aminopyridine
4-aminopyridine
2-aminoquinoline
2-fluorenamine
2-amino-3-nitro-5-methylsulfonamidothiophene
5-aminobarbituric acid and its derivatives
2-aminocarbazole
3-aminophthalic acid N-ethyl imide The formula $B(OH)_n$ wherein B and $n$ are as above defined designates a coupling component which is free of any solubilizing sulfonic and carboxylic acid groups. $n$ may be 0 in the coupler component where n in the diazo moiety is 1 or 2 and vice versa.

Compounds which are capable of coupling and which will form quaternary ammonium compounds according to the method of the invention also include di(hydroxyethoxy)resorcinol and a barbituric acid derivative having the formula:

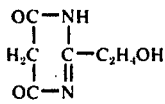

A particularly valuable class of dyestuffs for use in the invention corresponds to compounds wherein $B\text{-}(OH)_n$ represents aniline or a substituted aniline derivative which is capable of coupling in the para position to the amine substituent are characterized by the following formula:

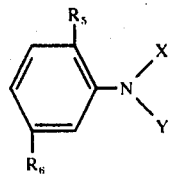

wherein $R_6$ represents hydrogen, methyl, lower alkoxy, chloro, bromo, lower acyl, or benzoyl amido; $R_5$ represents hydrogen, methyl, or lower alkoxy and X and Y each represents hydrogen, lower alkyl or substituted lower alkyl, wherein said substituent is chlorine, bromine, fluorine, cyano, hydroxy, lower alkoxy, carboalkoxy, carbamyl, hydroxy lower alkoxy, lower alkoxy lower alkoxy or the like.

Illustrative of the compounds corresponding to the above formula are the following:
- N-methyl, ethyl, propyl, isopropyl, butyl, tert-butyl, amyl and hexylaniline and the N,N-dialkyl derivatives thereof
- 2-chloroethyl and di(2-chloroethyl)aniline
- 2-cyanoethylaniline
- 2-bromoethylaniline
- 2-fluoroethylaniline
- 2-chloroethyl-2-cyanoethylaniline
- 2-hydroxyethyl and di(2-hydroxyethyl)aniline
- 3-hydroxypropyl and di(3-hydroxypropyl)aniline
- di-(2-methoxyethyl)aniline
- di-(2-ethoxyethyl)aniline
- di-(2-hydroxy-ethoxyethyl)aniline
- di-(2-methoxyethoxyethyl)aniline
- di-(2-ethylcarbamylethyl)aniline
- di-(2-carboethoxyethyl)aniline
- (acetoxyethyl)ethylaniline
- 3-chloro-di-(2-hydroxyethyl)aniline
- 3-bromo-di-(2-hydroxyethyl)aniline
- 3-fluoro-di-(2-hydroxyethyl)aniline
- 3-methyl-di-(2-hydroxyethyl)aniline
- 3-methoxy-ethyl-(2-hydroxyethyl)aniline
- 3-acetamido-di-(2-hydroxyethyl)aniline
- 3-butyramido-di-(2-hydroxyethyl)aniline
- 3-benzamido-di-(2-hydroxyethyl)aniline
- 3-toluoylamido-di-(2-hydroxyethyl)aniline
- 2-methoxy-di-(2-hydroxyethyl)aniline
- 2-methoxy-5-methyl-di-(2-hydroxyethyl)aniline Suitable organic sulfonyl halides for use in carrying out the process of the invention include the following:
- methylsulfonyl chloride
- ethylsulfonyl chloride
- propylsulfonyl chloride
- butylsulfonyl chloride
- hexylsulfonyl chloride
- trichloromethylsulfonyl chloride
- trifluoromethylsulfonyl chloride
- phenylsulfonyl chloride
- p-tolylsulfonyl chloride
- p-bromophenylsulfonyl chloride
- 2-naphthylsulfonyl chloride
- methylsulfonyl bromide
- methylsulfonyl fluoride Examples of the tertiary amines which may be employed as quaternizing agents are the following:
- trimethylamine
- triethylamine
- tripropylamine
- tri-isopropylamine
- tributylamine
- tri-tert-butylamine
- triamylamine
- trihexylamine
- diethylmethylamine
- dipropylmethylamine
- pyridine
- picoline
- quinoline and the like The quaternary ammonium compound according to the invention are prepared employing about one equivalent of the hydroxy compound which is to be quaternized, a slight excess of sulfonyl chloride up to about 10% equimolar excess and about 2-5 equivalents of the tertiary amine. The compounds to be reacted are combined and heated to effect quaternization. Heating at reflux is preferred for a period of about 1 to 10 hours. The reflux temperature varies for each system. However, if desired, lower temperaures, for instance as low as about 70° C., may be utilized, but operating at such low temperatures requires a longer reaction time.

The quaternization may be effected in the presence of a solvent and specifically of a solvent which is inert with respect to the reactants and the products. Suitable solvents include, for example, benzene, toluene, xylene, chlorobenzene, chloroform and the like. Excess amine may be used in lieu of solvent. The quaternization products formed are water-soluble and can be isolated either by cooling to precipitate and filtering; by evaporating off the solvent; by mixing with water and salting out, or by drowning in an organic solvent such as benzene to precipitate out the product.

In the production of azo dyestuffs, the process of the invention may be varied so that the hydroxyalkyl-containing intermediate is first treated with the sulfonyl chloride and tertiary amine to produce the quaternized diazo base or coupler following which the diazo base is diazotized and coupled with the coupler to produce the quaternized azo dyestuff product.

The following examples are given in order to more fully illustrate the invention but are in nowise to be construed as limiting the scope thereof.

EXAMPLE 1

Preparation of an orange dyestuff having the formula:

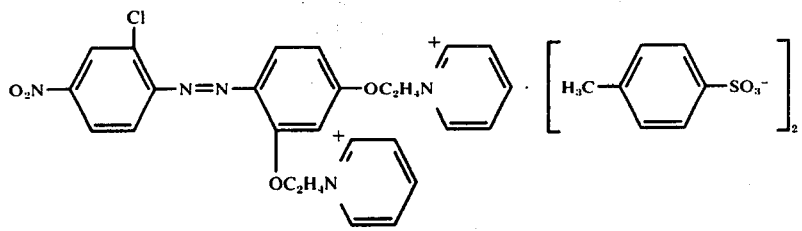

38 g. (2 moles) p-toluenesulfonyl chloride were added to a solution of 18.2 g. (0.05 mole) of the compound having the formula:

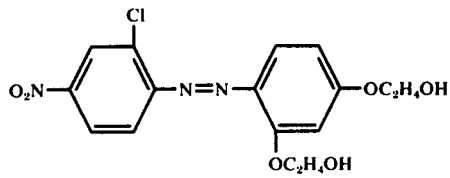

in 100 g. pyridine at room temperature. The mixture was heated to reflux and refluxed for 2 hours. A clear, deep red solution was thereby obtained. On dilution with water, no precipitation took place establishing the water-solubility of the product. Addition of benzene to the solution caused precipitation. Following removal of the solvent by distillation and cooling, there remained a sandy precipitate which was insoluble in benzene but was soluble in water. Thin layer chromatography (TLC) and infra red analysis established the identity of the product. In use, dyeings of good fastness to light and washing were obtained.

EXAMPLE 2

Preparation of a red dyestuff having the formula:

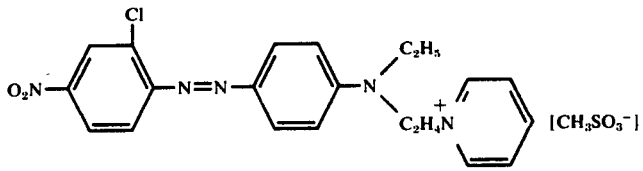

30 g. of the dyestuff having the formula:

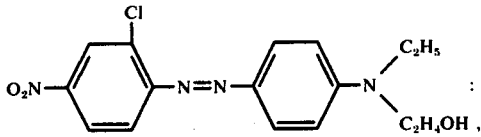

70 ml. pyridine and 15 g. methylsulfonyl chloride were combined and heated to reflux and maintained under reflux for about 15 hours. A very small amount of an intermediate was still present as indicated by TLC. The reaction mixture was cooled to 50° C., filtered, washed with 15 ml. cold pyridine and dried. The yield amounted to 120% of theory. The dyestuff thus produced had excellent qualities of purity, strength and fastness in use.

EXAMPLE 3

Preparation of a yellow dyestuff having the formula:

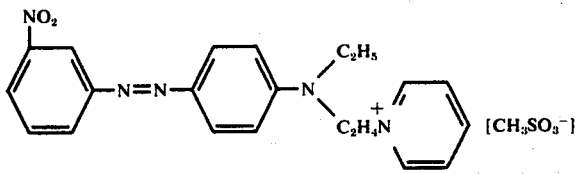

26.5 g. of the dyestuff having the formula:

100 ml. pyridine and 13 ml. methylsulfonyl chloride were combined, heated to reflux and refluxed overnight. When the reaction mixture was subjected to TLC analysis in the morning, the reaction was found to be complete. The product was cooled, filtered and washed with cold pyridine. 41.5 g. (dry weight) of the product having the above formula were obtained.

EXAMPLE 4

Preparation of a red dyestuff having the formula:

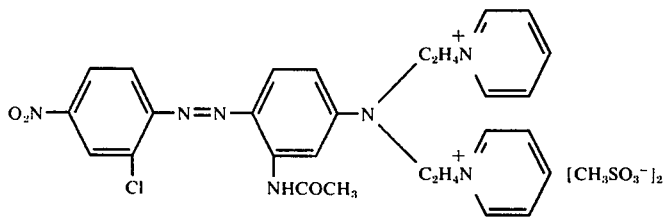

42.5 g. of the dyestuff having the formula:

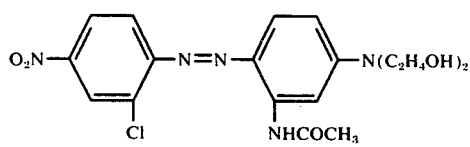

100 ml. pyridine and 30 ml. methylsulfonyl chloride were combined. The reaction proceeded exothermically and cooling was necessary in order to keep the temperature below 90° C. A solid product formed which liquified on heating to reflux. Additional pyridine was added, but solidification occurred again. The product was cooled and washed with 50 ml. cold pyridine yielding a product having a dry weight of 84.5 g. The product was water soluble, producing a red solution and was particularly useful in the dyeing of cationically dyeable fibers.

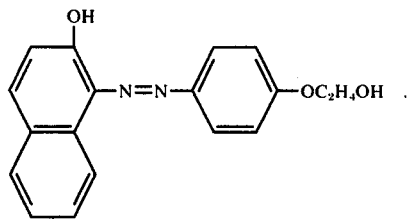

were dissolved in 100 ml. pyridine. 22 ml. methylsulfonyl chloride were added slowly under maintenance of the temperature at 65° C. The reaction mixture was then refluxed for 12 hours, cooled slowly and filtered. The solid material separated off and was dried to give a dry weight of 61 g.

EXAMPLE 6

Preparation of a yellow dyestuff having the formula:

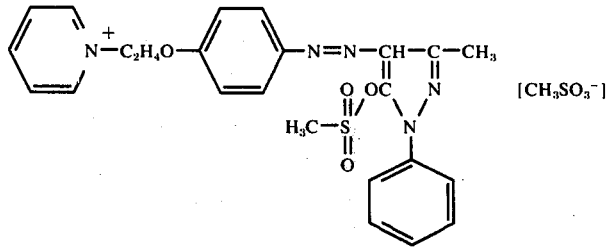

EXAMPLE 5

Preparation of an orange dyestuff having the formula:

36 g. of the dyestuff having the formula:

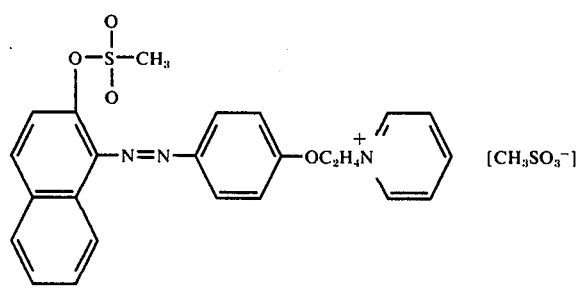

27 g. of the dyestuff having the formula:

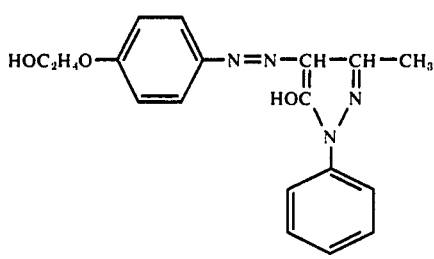

were mixed with 150 ml. pyridine. There were then added in dropwise fashion 16 ml. methylsulfonyl chloride. At 65° C. all of the base had gone into solution. The solution was refluxed for a total of 12 hours, cooled, filtered and dried, yielding a granular product amounting to 48 g. dry weight which dyed cationically dyeable fibers a green yellow.

EXAMPLE 7

Preparation of a yellow dyestuff having the formula:

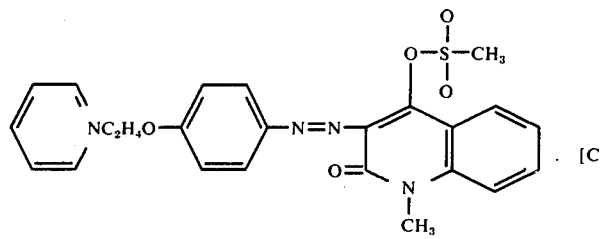

34 g. of the dyestuff having the formula:

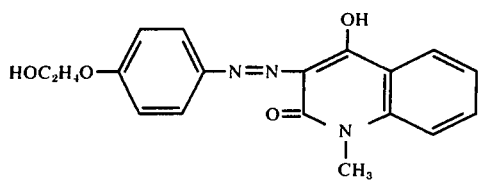

and 175 ml. pyridine were mixed together. 16 ml. methylsulfonyl chloride were added slowly, and the resultant mixture warmed. At 70° C., the base had gone completely into solution. It was refluxed overnight, cooled, filtered, washed with cold pyridine and dried. The product recovered had a dry weight of 35 g. and and gave intense green yellow dyeings of good fastness.

EXAMPLE 8

Preparation of a yellow dyestuff having the formula:

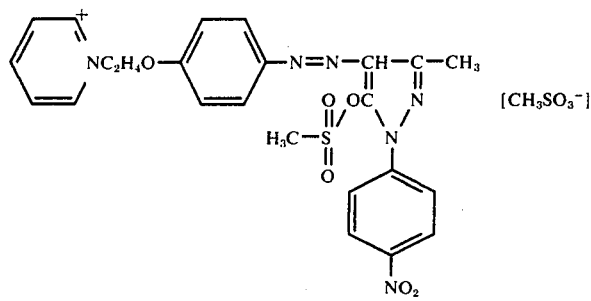

39.5 g. of the dyestuff having the formula:

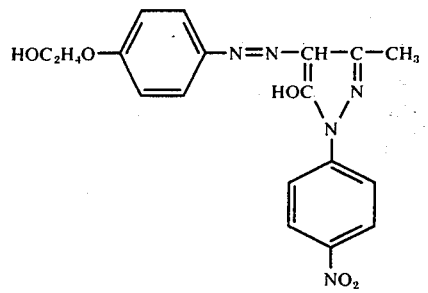

were admixed with 100 ml. pyridine. There were slowly added to the mixture 16 ml. methylsulfonyl chloride and this mixture heated to reflux and refluxed for 4 hours. Following cooling, filtering, washing with pyridine and drying, the product having the above formula was recovered.

EXAMPLE 9

Preparation of a pale yellow dyestuff having the formula:

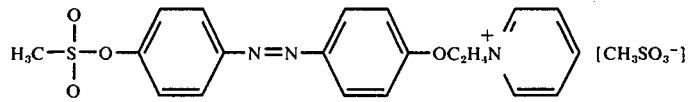

25.5 g. of the dyestuff having the formula:

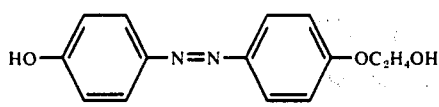

and 100 ml. pyridine were combined at room temperature. 17 ml. methylsulfonyl chloride were then added dropwise under conditions whereby the temperature did not rise about 85° C. The reaction mixture was then refluxed for 18 hours, cooled, filtered and washed with cold pyridine. The product recovered had a dry weight of 15 g.

EXAMPLE 10

Preparation of laurylpyridinium methyl sulfonate

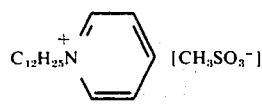

5 ml. lauryl alcohol, 25 ml. benzene, 25 ml. pyridine and 2½ ml. methylsulfonyl chloride were combined and the resultant mixture heated to reflux for 3 hours. Thin layer chromatography showed complete quaternization. Cooling to room temperature gave a water-soluble precipitate which was useful as a surfactant.

EXAMPLE 11

Preparation of a quaternized nonylphenoxypoly(ethyleneoxy) ethanol, Igepal (registered trademark) CO630 supplied by GAF Corp.

5 ml. nonylphenoxypoly(ethyleneoxy) ethanol and 50 ml. pyridine were combined. There were then added 2½ ml. methylsulfonyl chloride and the mixture heated to reflux. Thin layer chromatography showed complete quaternization after 3 hours. on cooling to room temperature, the product comprising clear, colorless, water-soluble crystals was obtained which was useful as a surfactant.

EXAMPLE 12

Preparation of cetyl pyridinium methyl sulfonate.

20 g. of cetyl alcohol Lorol (registered trademark) 24, supplied by du Pont E. I. de Nemours and Co., Inc. pyridine were admixed and 15 ml. methylsulfonyl chloride were then added slowly to the mixture. A precipitate formed which on heating of the mixture to reflux dissolved. Thin layer chromatography established complete quaternization after 3 hours. On cooling to room temperature a solid material formed which was filtered, washed with cold pyridine and dried. The solid product was water-soluble, but insoluble in benzene. This material acts as an inhibitor against gram negative and gram positive bacteria.

EXAMPLE 13

The dyestuff of Example 2 was prepared, with the exception that the methylsulfonyl chloride was replaced by an equivalent amount of p-bromobenzenesulfonyl chloride. The quaternization required a longer time, but a completely quaternized product was obtained.

EXAMPLE 14

The dyestuff of Example 2 was prepared using the procedure of that example with the exception that the methylsulfonyl chloride was replaced by an equivalent amount of 2-naphthalenesulfonyl chloride. The quaternization required a longer time, but a completely quaternized product was obtained.

EXAMPLE 15

Example 2 was repeated, with the exception that the methylsulfonyl chloride was replaced by an equivalent amount of butylsulfonyl chloride. A dye with substantially the same properties was obtained.

EXAMPLE 16

Preparation of a dyestuff having the formula:

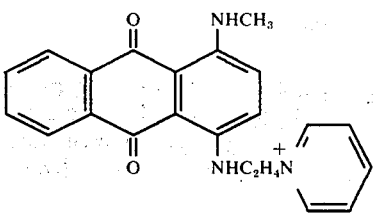

29.6 g. 1-(2-hydroxyethylamino)-4-methylaminoanthraquinone were dissolved in 100 ml. pyridine. 9 ml. methylsulfonyl chloride were then added dropwise so that the temperature did not exceed 5° C. The resultant mixture was heated under reflux for 12 hours, cooled and filtered. The filter cake was washed with cold pyridine and dried to give a blue water-soluble dye having a dry weight of 44 g.

EXAMPLE 17

Example 2 was repeated with the exception that the methanesulfonyl chloride was replaced by 22.5 g. methanesulfonyl bromide. The results were substantially the same.

EXAMPLE 18

Example 2 was repeated with the exception that the methanesulfonyl chloride was replaced by 13.3 methanesulfonyl fluoride. The results were commensurate with those obtained in Example 2.

EXAMPLE 19

Orlon polyacrylonitrile fiber was dyed as follows:
Aqueous dyebaths were prepared containing 1, 2, 3, 4, 5 and 6% of the dyestuff of Example 2 (based on the weight of the fiber) respectively. A goods-to-liquor ratio of 1:40 was employed. 3% acetic acid, based on the weight of the fiber was added. Three gram swatches of material were introduced into the baths and they were brought to the boil within 20–30 minutes. The boiling was continued for 1 hour. The swatches were then removed, rinsed and dried. Bright red dyeings were obtained. The build-up and exhaust properties were excellent. The light fastness was very good and the pH stability especially good under highly acid conditions.

These swatches were then cut into 4 pieces each and the smaller swatches boiled in baths at pH 2, 4, 6 and 8 respectively. There was no change in shade or strength in all cases, demonstrating the lack of sensitivity to pH change of the dyed fibers.

What is claimed is:

1. A method for preparing a quaternary pyridinium product compound having the formula:

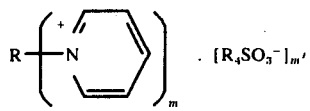

wherein R represents alkyl,

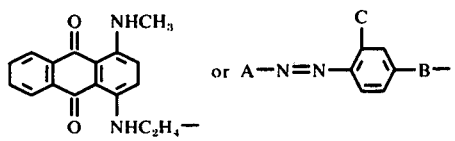

in which A is phenyl, naphthyl, carbostyrilyl, pyrazolinyl and substituted derivatives thereof where the substituents are selected from the group consisting of methyl, $NO_2$, Cl, phenyl, nitrophenyl and methyl sulfonate; B is -O-ethylene-,

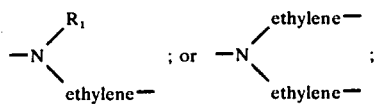

and C is selected from the group consisting of H, $NHCOCH_3$ and, when B is -O-ethylene-, C can also be $—OC_2H_4—$, where $R_1$ is methyl or ethyl, and wherein $R_4$ represents alkyl having 1 to 4 carbon atoms, bromophenyl, methylphenyl or naphthyl; m represents an integer of 1 or 2 and m' is equal to m, which comprises: contacting pyridine and a hydroxy-containing compound having the formula: $R'—(OH)_n$ wherein $R'$ represents alkyl,

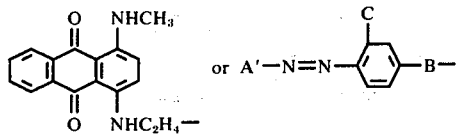

in which $A'$ is phenyl, naphthyl, carbostyrilyl, pyrazolinyl and substituted derivatives thereof where the substituents are selected from the group consisting of methyl, $NO_2$, Cl, phenyl, nitrophenyl and hydroxy, and n is an integer of 1 or 2 and is equivalent to m defined above, and B and C are as defined above; reacting the pyridine and said hydroxy-containing compound in the presence of a sulfonyl halide having the formula: $R_4SO_2X$ wherein $R_4$ is as defined above and X is Cl, Br or F; and conducting the reaction at an elevated temperature up to the reflux temperature of the reaction mixture.

2. A method for preparing quaternary pyridinium compound which comprises: contacting pyridine and an azohydroxy compound containing not more than 2 hydroxy groups and having the formula:

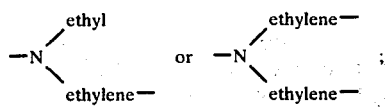

wherein $A'$ is phenyl, naphthyl, carbostyrilyl, pyrazolinyl and substituted derivatives thereof where the substituents are selected from the group consisting of methyl, hydroxy, $NO_2$, Cl, phenyl and nitrophenyl; B is -O-ethylene-,

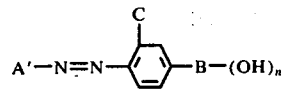

C is hydrogen, $NHCOCH_3$ or, when B is -O-ethylene-, C can also be -O-ethylene-OH and n is an integer of 1 or 2; reacting the pyridine and said azo-hydroxy compound in the presence of a sulfonyl halide having the formula: $R_4—SO_2X$ wherein $R_4$ is alkyl of 1 to 4 carbon atoms, bromophenyl, methylphenyl or 2-naphthyl and X is Cl, Br or F; and conducting the reaction at an elevated temperature up to the reflux temperature of the mixture.

* * * * *